(12) United States Patent
Duffy

(10) Patent No.: US 8,375,529 B1
(45) Date of Patent: Feb. 19, 2013

(54) TOUCH ENGAGEABLE FASTENER

(76) Inventor: Leonard Arnold Duffy, Hinesburg, VT (US)

( * ) Notice: Subject to any disclaimer, the term of this patent is extended or adjusted under 35 U.S.C. 154(b) by 673 days.

(21) Appl. No.: 12/462,040

(22) Filed: Jul. 27, 2009

Related U.S. Application Data

(60) Provisional application No. 61/137,420, filed on Jul. 29, 2008, provisional application No. 61/207,007, filed on Feb. 6, 2009.

(51) Int. Cl.
*A44B 1/04* (2006.01)

(52) U.S. Cl. .......................................................... 24/452

(58) Field of Classification Search .................... 24/452, 24/449, 450
See application file for complete search history.

(56) References Cited

U.S. PATENT DOCUMENTS

| | | | |
|---|---|---|---|
| 2,727,437 A | 9/1955 | Demestral | |
| 3,266,113 A | 8/1966 | Flanagan | |
| 3,372,442 A | 3/1968 | Ishimatsu | |
| 3,408,705 A | 11/1968 | Kayser et al. | |
| 3,522,637 A | 8/1970 | Brumlick | |
| 3,594,863 A | 7/1971 | Erb | |
| 3,604,145 A | 9/1971 | Zimmerman | |
| 3,808,648 A * | 5/1974 | Billarant et al. | 24/450 |
| 3,961,398 A | 6/1976 | Herterich et al. | |
| 4,169,303 A | 10/1979 | Lemelson | |
| 4,322,875 A | 4/1982 | Brown | |
| 4,531,733 A | 7/1985 | Hall | |
| 4,581,792 A | 4/1986 | Spier | |
| 4,870,721 A | 10/1989 | Cohen | |
| 4,875,259 A | 10/1989 | Appledorn | |
| 4,946,527 A | 8/1990 | Battrell | |
| 5,067,210 A | 11/1991 | Keyaki | |
| 5,088,162 A | 2/1992 | Alan | |
| 5,088,164 A | 2/1992 | Wilson et al. | |
| 5,119,531 A | 6/1992 | Berger et al. | |
| 5,201,101 A | 4/1993 | Rouser | |
| 5,212,853 A | 5/1993 | Kaneko | |
| 5,212,855 A | 5/1993 | Mcganty | |
| 5,221,276 A | 6/1993 | Battrell | |
| D340,007 S | 10/1993 | Gershenson | |
| 5,312,456 A * | 5/1994 | Reed et al. | 411/456 |
| 5,360,270 A | 11/1994 | Appledorn | |
| 5,396,687 A | 3/1995 | Osterman | |
| 5,457,856 A | 10/1995 | Murasaki | |
| 5,460,769 A | 10/1995 | Kaneko | |
| 5,505,747 A | 4/1996 | Chasley et al. | |
| 5,586,372 A | 12/1996 | Eguchi | |
| 5,596,794 A | 1/1997 | Shibanushi | |

(Continued)

FOREIGN PATENT DOCUMENTS

| | | |
|---|---|---|
| AU | 199857147 | 7/1998 |
| CA | 2311306 | 5/2000 |

(Continued)

*Primary Examiner* — Robert J Sandy
*Assistant Examiner* — Matthew Sullivan

(57) ABSTRACT

A self-engaging touch fastener, separable by peeling, includes portions with a generally thin shell structure and a closely spaced array of bilaterally undercut generally convex protrusions which are directed by proximate oblique stem walls into an interlocking relationship with corresponding receptors when the portions are compressed. Touch fastening products have a non-grabbing non-abrasive texture and may be manufactured of thin plastic films or similar low cost materials using a simple die-cutting/forming method, thus providing a user friendly reliable and economic alternative to hook-and-loop and other presently available fastening systems for connecting flexible materials for applications including packaging, apparel, and disposable products. The device may be furnished as an independent product, as an integrally formed or molded segment of a primary product, or attached to rigid or flexible substrates. An apparatus and method for economically manufacturing such device is also provided.

22 Claims, 7 Drawing Sheets

U.S. PATENT DOCUMENTS

Figure 1:
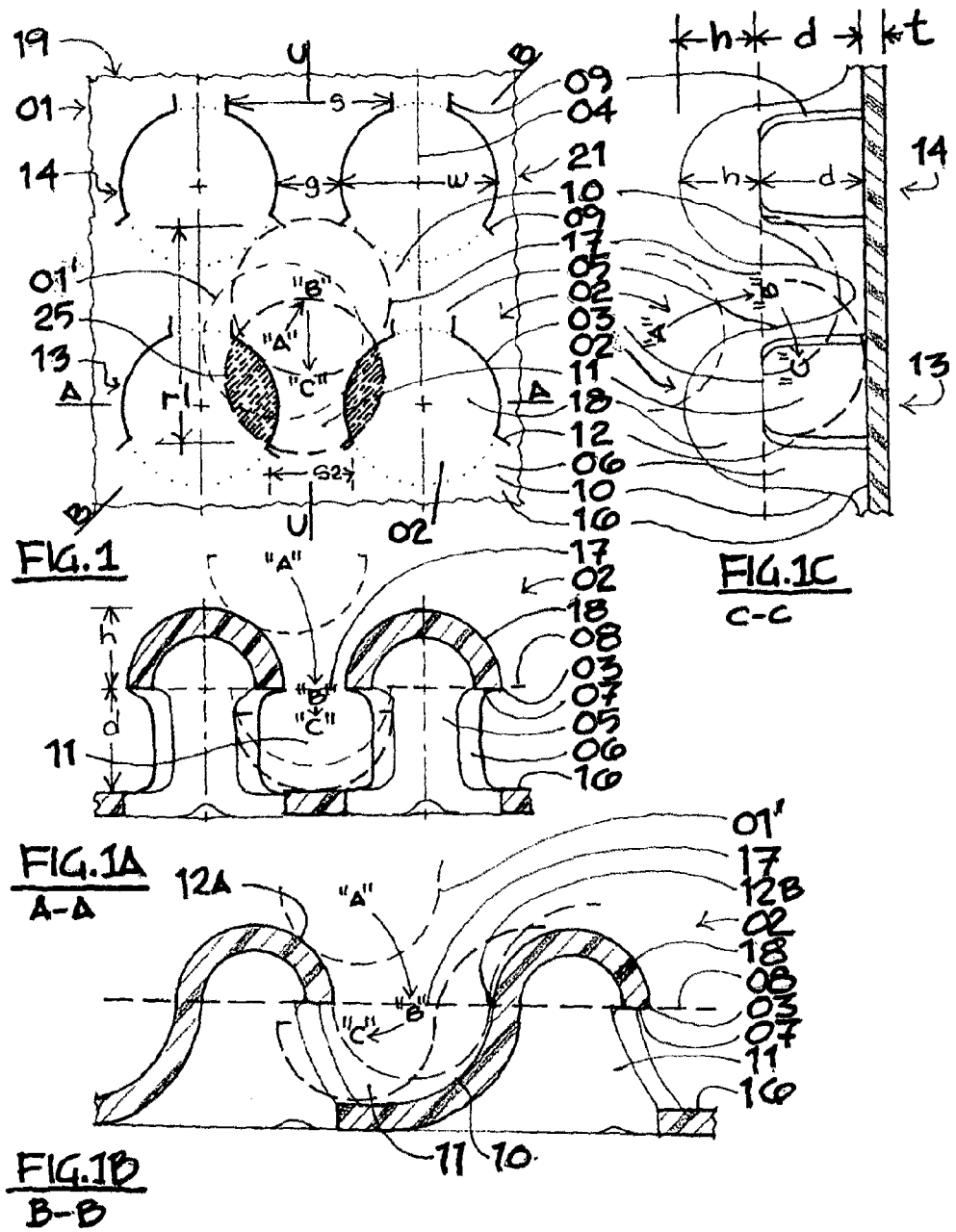

| | | | |
|---|---|---|---|
| 5,614,232 | A | 3/1997 | Torigoe et al. |
| 5,622,578 | A | 4/1997 | Thomas |
| 5,624,427 | A | 4/1997 | Bergman et al. |
| 5,625,929 | A | 5/1997 | Hattori et al. |
| 5,657,516 | A | 8/1997 | Berg et al. |
| 5,713,111 | A | 2/1998 | Hattori et al. |
| 5,735,840 | A | 4/1998 | Kline et al. |
| 5,755,015 | A | 5/1998 | Akeno et al. |
| 5,799,378 | A | 9/1998 | Gershenson |
| 5,813,095 | A | 9/1998 | Robertson |
| 5,867,876 | A | 2/1999 | Petersen |
| 5,902,427 | A | 5/1999 | Zinke et al. |
| 5,983,467 | A * | 11/1999 | Duffy .............................. 24/442 |
| 5,987,706 | A | 11/1999 | Boe |
| 6,059,558 | A | 5/2000 | Buzzell et al. |
| 6,076,238 | A | 6/2000 | Arsenault et al. |
| 6,162,040 | A | 12/2000 | Clune |
| 6,223,401 | B1 | 5/2001 | D'Sa et al. |
| 6,526,633 | B2 | 3/2003 | Provost |
| 6,687,962 | B2 | 2/2004 | Clarner et al. |
| 7,036,190 | B2 | 5/2006 | Demarest |
| 7,241,483 | B2 | 7/2007 | Ausen |
| 7,254,874 | B2 | 8/2007 | Duffy |
| 2008/0034560 | A1 | 2/2008 | Duffy |
| 2009/0106953 | A1 * | 4/2009 | Wittig ............................. 24/442 |
| 2009/0126165 | A1 * | 5/2009 | West .............................. 24/449 |
| 2009/0126166 | A1 | 5/2009 | Tuma |

FOREIGN PATENT DOCUMENTS

| | | |
|---|---|---|
| GB | 1011362 | 4/2003 |

* cited by examiner

TOUCH ENGAGEABLE FASTENER

PRIORITY

This application claims priority on the basis of US provisional patent applications: 61/137,420, filed Jul. 29, 2008; and 61/207,007, filed Feb. 6, 2009.

FIELD

This application is related to touch-type surface fasteners with hermaphroditic portions.

BACKGROUND

The field of Touch fasteners includes many well known products manufactured under the trade names of Velcro®, Aplix®, YKK®, 3M®, and others. Generally these systems include hook-and-loop types with differentiated portions, or self-engaging types with hermaphroditic portions, each type having well known attributes as well as known drawbacks. Abrasion, clogging, noise, lack of durability, failure when wet, loss of strength, indiscriminate grab, profile thickness, and relative cost are all frequently cited negative attributes of hook-and-loop systems. Mushroom systems and others share similar negative attributes and are limited by the excessive force needed for disengagement and limited cycle life. With regard to disposable products in particular, cost and type of material are significant factors. Abrasion, relative to products in contact with skin, as well as noise are also significant issues for many applications such as personal care products.

Examples of fabric based hook-and-loop fasteners include: DeMestral U.S. Pat. No. 2,717,437; Erb U.S. Pat. No. 3,594,863, Zinke et al U.S. Pat. No. 4,910,062, and Brumlik, U.S. Pat. No. 3,522,637. Examples of molded hook-and-loop hooks include: Kayaki, U.S. Pat. No. 5,067,210, Berger et al, U.S. Pat. No. 5,119,531; and Provost, U.S. Pat. No. 6,526,633. Examples of self-engaging undercut mushroom-like fasteners include: Flanagan, U.S. Pat. No. 3,666,113; Hall, U.S. Pat. No. 4,531,733; and Tuma US2009/0126166 A1. Examples of interengaging bulbous shapes include: Batrell, U.S. Pat. No. 4,946,527, Petersen, U.S. Pat. No. 5,867,876; Clume, U.S. Pat. No. 6,162,040. Chesley et al., U.S. Pat. No. 5,505,747 disclose hooks and mushrooms of various profiles. The prior art also includes other types of interengaging three dimensional shapes, examples of which include: Rouser, U.S. Pat. No. 5,201,101; Murasaki, U.S. Pat. No. 5,457,856; McGanty, U.S. Pat. No. 5,212 855; Berg, et al, U.S. Pat. No. 5,657,516; and Appledorn, U.S. Pat. No. 4,875,259. Ausen, U.S. Pat. No. 7,241,483, more recently discloses a reticulating web with hooks formed by a multiple step process. All typically include a plurality of male to male members locking with multidirectional undercuts or by friction.

Several examples of prior art include relatively thin structures which are formed into fastening elements. Zimmerman, U.S. Pat. No. 3,604,145, discloses a strip of sheet material formed into nesting frictionally connected pins/receptors. Spier, U.S. Pat. No. 4,581,792, discloses a sheet formed unidirectionally undulating structure which is self-engaged by friction along its alternating undulated edges. Cohen, U.S. Pat. No. 4,870,721, discloses hollow pyramids with barbs for fastening with a second receiving structure. Battrell, in U.S. Pat. No. 4,946,527 and U.S. Pat. No. 5,221,276, presents interengaging portions with pluralities of three-dimensionally bulbous shapes with hollow inner cores, apparently formed from a sheet material: the portions are interengaged by compression causing respective bulbous heads to deform and then expand so that their inclined underwalls interface.

Fastening Technologies, including slidingly engaging fasteners and several improvements thereto were introduced by the present inventor, as disclosed in U.S. Pat. Nos. 5,983,467, 7,245,416, AU Patent 60/034,096, EPO Patent 1,011,362, CA Patent 2, 311,306, and other patents pending including Published US application 2008/0018025 A1 concerning methods of making fasteners including die forming methods. Slidingly engaging fasteners (SEFs) comprise generally hermaphroditic arrays of islands with undersides and corresponding receiving apertures between adjacent islands. The islands are connected by sliding correspondent undersides beneath each other until they are stopped at the narrow end of an effectively tapered chamber. Some of the previously disclosed embodiments of SEFs also have included three-dimensional surface modeling to enhance self-alignment, spacing of islands to prevent back sliding, as well as three dimensional aspects to enhance initiation of engagement by compression. However, the thickness of islands is generally equal to the depth of corresponding apertures so that at least minimal shear pressure is required to achieve engagement. For some applications requiring significant flexure, low cost production, relatively small scales, and engagement by simple compression (touch), these previous SEF systems may be less than fully adequate. In particular, an SEF system which is fully self-aligned, which can be engaged solely by touch, which has a generally undulating texture with no exposed edges, and which can be produced of inexpensive materials by die forming would be particularly useful.

A pressure activated self-adhering device also by the present inventor has been published as US 2008/0034560 A1. It includes a plurality of nodules protruding from the interstices of a structural matrix which define receptors for receiving like modules to effect a very low-profile self-engaging fastener with no additive thickness. This system however requires relatively significant compressive engagement pressure and is preferably manufactured by a relatively expensive molding process.

There appears to be a continuing significant need and market for an improved type of self-engaging touch fastener which is easy to use, relatively durable, quiet, non-abrasive to skin, and which could be manufactured at low cost by die cut and formed materials including plastic films.

GENERAL DESCRIPTION

A primary object of the present invention is to provide an economical alternative to presently available touch fasteners which is non-grabbing, smooth to touch, strong, quiet, hermaphroditic, and inexpensive to manufacture. Other objects of this invention include providing a touch engageable fastener: which has a non-grabbing texture; which is soft to touch; which is economical to produce by die forming sheet materials; which securely connects portions with a relatively light touch; which is resistant to aggregate tensile stresses but easily peeled apart from a joining portion end; which is substantially resistant to shear, tensile, and torque forces; which is quiet; which is self-engaging with hermaphroditic portions; and which can be provided at virtually any scale and in a variety of embodiment designs. Further objects will become apparent throughout the disclosure.

The Touch Engageable Fastener includes two similar portions, each having an array of bilaterally undercut convex protrusions with fore and aft stems, defining receptors between each pair of protrusions which are deeper than the height of protrusions and also longer than protrusions, extending from a proximate stem wall. The protrusions are arranged so that, when the portions are lightly pressed together by a relative compressive force (touch), the protrusions of a first portion self-align with and are snuggly received into the corresponding receptor openings of a second portion. Upon continuing compression the protrusions are then diverted longitudinally into an effectively interlocked position by obliquely sloping stem walls and entrapped within respective corresponding receptors. The assembled portions are resistant to longitudinal or lateral shear as well as tension, but can be readily disconnected by simply applying tension to a lateral edge of one portion and sequentially reversing the connection process by peeling. In several preferred embodiments the fastener portion is presented as an effectively dimpled, undulating surface made up of a plurality of dome-like protrusions, thereby providing a generally soft surface texture with blind fastening elements. Alternative geometric configurations are also included.

In each embodiment, receptors are at least somewhat deeper than corresponding protrusions, and stem walls are obliquely inclined, so that after the protrusions pass through their respective receptor openings, continuing perpendicular touch pressure causes the protrusions to shift longitudinally within the receptor until respective protrusion undersides oppose each other to effect a secure interlocking connection.

Touch Engageable Fasteners of a first preferred embodiment have receptor openings sized to just snugly receive corresponding protrusions without significantly distorting the structure and have a longitudinally asymmetrical design to resist applied uni-directional shear, thereby requiring minimal pressure to engage or disengage and causing minimal structural stress or sound. Touch fasteners of other embodiments include receptor openings which are somewhat smaller than corresponding protrusions and a longitudinally symmetrical design, so that, as compression is applied, interfacing protrusion sidewalls "snap" into respective openings, temporarily distorting to allow corresponding edges to bypass, resulting in an assembly resistant to bi-directional shear as well as tensile stresses.

The "snap" engagement attribute may be applied to embodiments of either symmetrical or asymmetrical design. In embodiments of the "snap" type, the depth to height differential allows bypassing undercut edges to distort vertically as they pass through respective receptor openings and to then resiliently assume their prior shape as the protrusion also shifts longitudinally.

Longitudinally asymmetrical touch fasteners include aft stems which are wider than forward stems, thereby effecting a longitudinally narrowing receptor so that leading undercut edges of protrusions are blocked by the second stems at a position of optimal underside interface. Rows of protrusions may be furnished either in aligned rows (quadrille pattern), wherein the protrusion sidewalls interface with two adjacent stem walls of the next row; or in offset rows (diamond pattern), wherein the protrusion sidewalls interface with a single stem wall. A "snap" engagement aspect may also be optionally combined with such an asymmetrical configuration to provide primary unidirectional shear resistance with effective "back-out" resistance.

Longitudinally symmetrical fasteners with a "snap" aspect and at least three alternately offset (diamond pattern) rows are configured in a longitudinally symmetrical configuration with fore and aft stems of effectively equal width, wherein the receptors are bounded and longitudinally aligned with the proximate protrusion stem walls of each adjacent offset row. This configuration combines bi-directional shear resistance with relatively short adjustment intervals. Such embodiments may be designed with relatively long receptors, in which protrusions are able to slide longitudinally when subjected to shear pressure; or they may be designed with relatively short receptors, close coupled, in which protrusions are longitudinally limited: the former requiring less engagement pressure, the latter providing a short adjustment interval. Such design choices must be based on application requirements and material characteristics.

Diverse geometric design options included within the scope of the invention provide optimal solutions for assorted application requirements. Design options include polygonal shapes, protrusions of diverse proportions including elongated and widened configurations, oblique undersides, and alternative geometries and combinations within the general parameters of the invention. Fasteners of the asymmetrically type are engaged with minimal touch pressure and are highly resistant to uni-directional and lateral shear, though they are less resistant to shear in a reversed (back-out) direction. Such fasteners are particularly suitable for applications affording relatively constant shear such as an elastic strap, or for a medical wrap or personal item, etc. where minimal pressure is also desirable. Fasteners of the "snap" type typically require somewhat greater compressive pressure in order to complete engagement and are therefore most suitable for applications requiring a secure connection where somewhat greater engagement force is tolerable such as in the closure for an apparel item, clothing accessory, footwear, packaging, etc. Fasteners of the "snap" type combined with a longitudinally symmetrical aspect may be best for applications requiring minimal shear strength such as various single use disposable products, plastic bags, packaging, etc. Because the device in any geometric variation is economical to produce at virtually any scale, a wide range of uses is foreseen in applications ranging from personal products, household goods, and personal electronic devices to high strength construction assemblies.

In general, a minimum of two rows of at least two protrusions are required on at least one of the portions to provide uni-directional shear resistance in the asymmetrical fasteners discussed above. Three rows are required to provide equal bi-directional shear resistance as in the symmetrical configuration above. In many applications, multiple rows are provided on at least one of the portions in order to maximize the range of adjustability. In some applications such as an integral closure for a sheet form plastic bag, a minimum number of rows is preferable.

Preferred embodiments of the device include a relatively thin generally flexible undulating structure with dome-like protrusions with edges extending partially over laterally adjacent receptors. The structure of such embodiments has a generally uniform thickness contiguous throughout the undulations except at its undercut edges. The fastener with its inherently closely spaced convex protrusions presents an effectively soft primary surface texture which is non-grabbing and non-abrasive (somewhat similar in texture to common "bubble wrap") which can be placed in close contact with skin or sensitive surfaces without causing abrasion, while the undercut undulations simultaneously provide an effective means of ventilating the underlying surface.

Embodiments of the device are produced at a relatively small scale by die forming thin sheet materials with a punching and forming dieset. Although such thin film materials are generally highly flexible in their unformed sheet state, those materials with satisfactory shape memory formed into a three-dimensional matrix of convex and concave forms become sufficiently rigid in their micro-structure to maintain repetitively reusable fastening function, resistant to crushing loads, while remaining flexible in the aggregate. In general, a material thickness to protrusion width ratio of 1:3 would appear to be a minimum practical limit, resulting in relatively stiff protrusions. Ratios of 1:10 and greater have been proven effective in prototypes. Such design choices are inherently related to material characteristics as well as application parameters.

When furnished as a flexible structural sheet with relatively small scale fastening modules, it is expected that an effective majority of the modules may will be fully connected and effective at a particular time. The aggregate redundancy of the system will be sufficient to maintain a strong connection of the whole even with some segments disconnected, a matter which may be determined by design.

In a preferred manufacturing method, a relatively thin plastic film, preselected for its inherent shape memory, is fed through a counter rotating dieset having punching and forming segments. The resultant fastening product can therefore be significantly less costly to produce than presently available molded, extruded or heat formed fastening systems.

Alternatively the device may be manufactured for many applications such as disposable products of paper or other fibrous matter by utilizing a similar counter rotating dieset into which a saturated pliable sheet or slurry is fed, the material dried as the fastening product is extracted. Another alternative means of manufacture comprises heat forming by feeding a softened semi-solid plastic sheet through a similar apparatus. Other manufacturing methods include: injection molding; punch and die forming sheet-metal embodiments; sequentially forming rows of fastening elements with a reciprocating punch and die apparatus; stamp/forming a pre-perorated sheet material; machining a solid substance; or other known means of manufacturing applicable to the present structural aspects. Alternative embodiments may be molded or formed of materials with differential thickness, for instance injection molded as an integral fastening zone in the surface of a primary product, molded of plastic or rubberized foams or fibrous materials, or simply machined in diverse materials by computerized machining tools.

DRAWINGS

FIG. 1 schematically represents a first preferred embodiment of a touch fastener portion in plan view. FIGS. 1A-C are sectional views.

Figure 2:
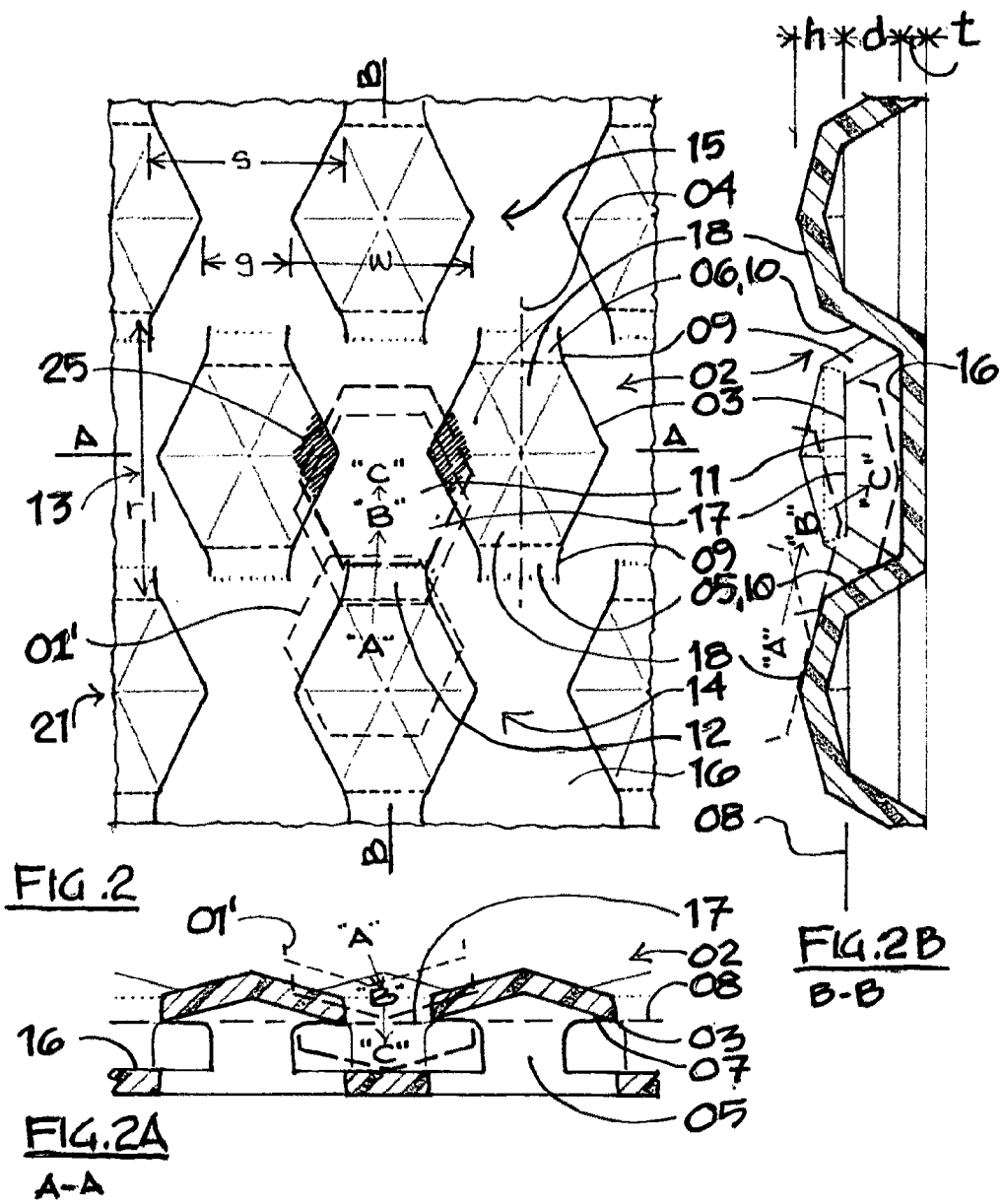

FIG. 2 schematically represents a second preferred embodiment of a touch fastener portion in plan view. FIGS. 2A-B depict sectional views.

Figure 3:
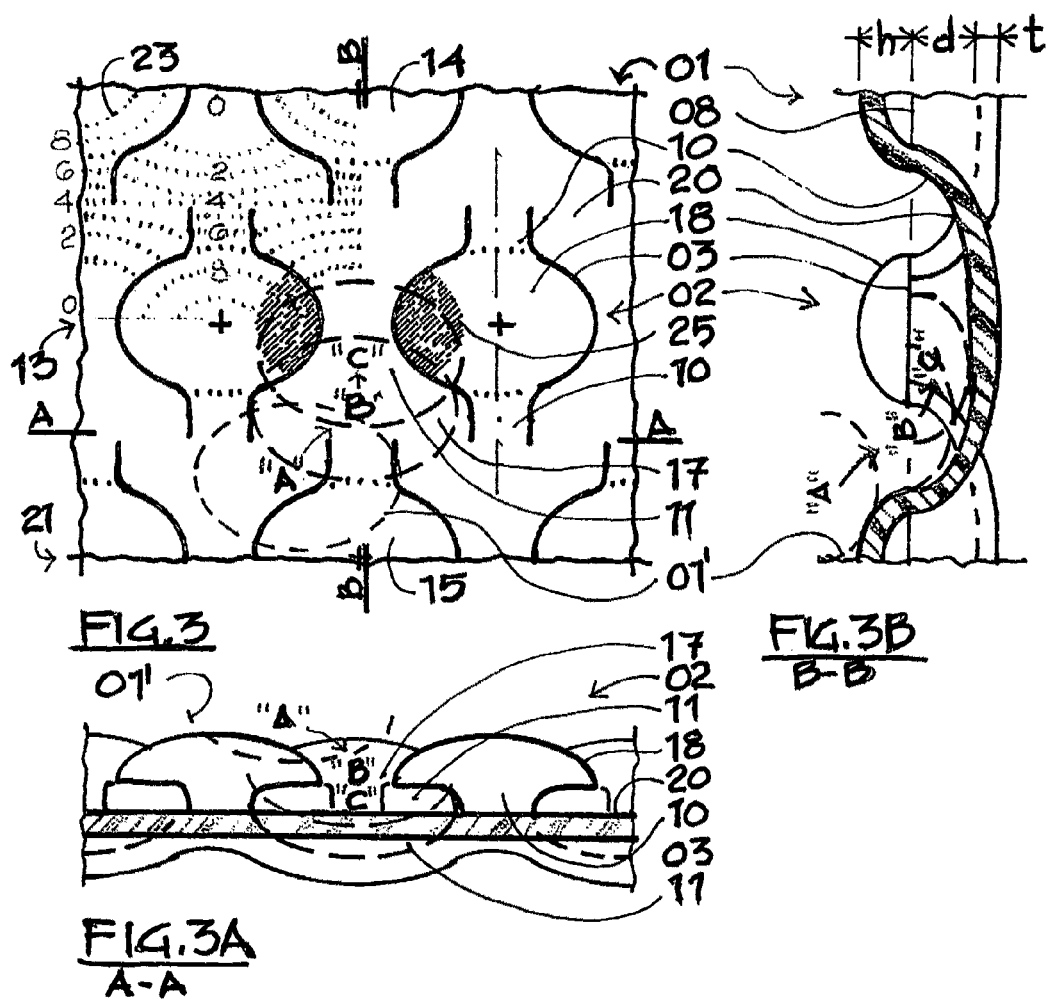

FIGS. 3, 3A and 3B schematically represent an alternative preferred embodiment of a touch fastener portion with elongated protrusions.

Figure 4:
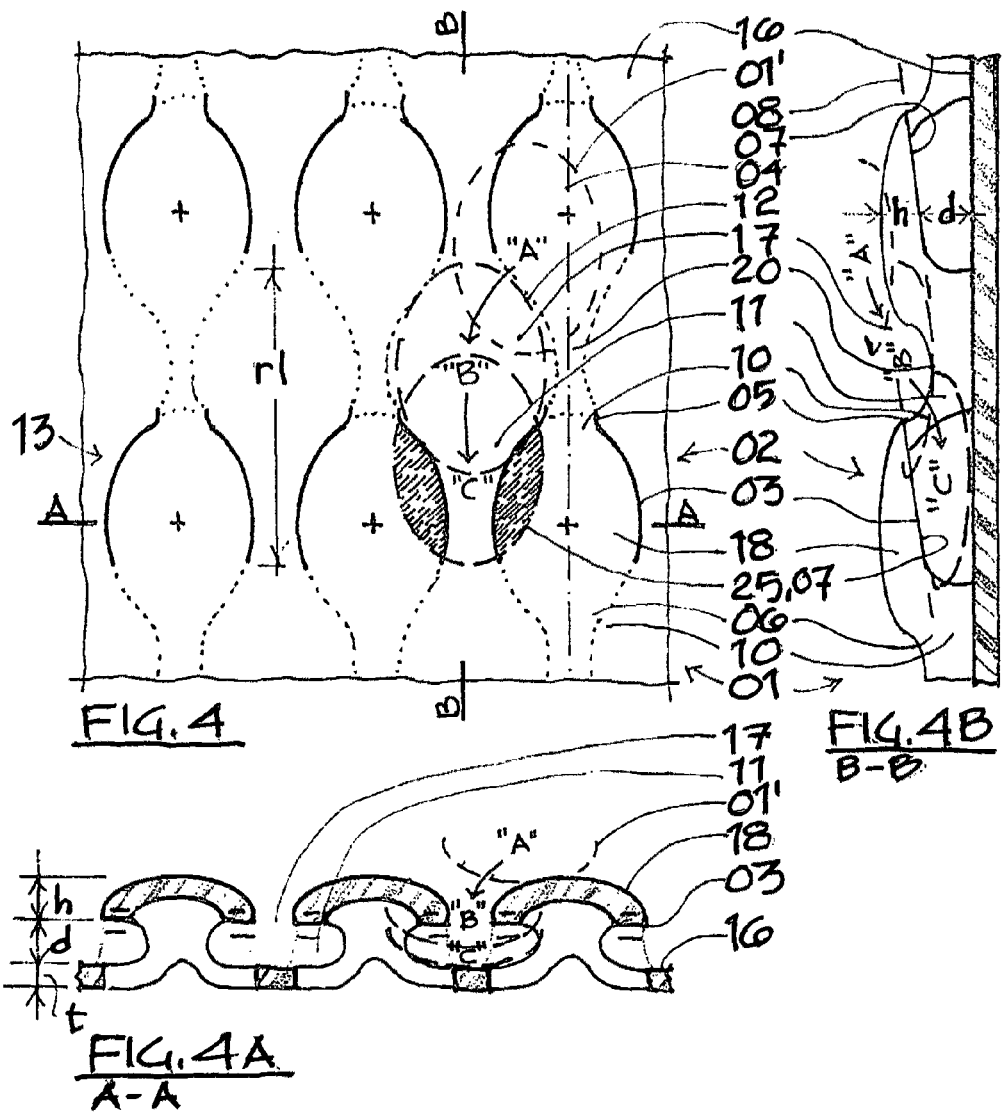

FIGS. 4, 4A, and 4B schematically represent an alternative preferred embodiment of a touch fastener portion with proportionally wide protrusions.

Figure 5:
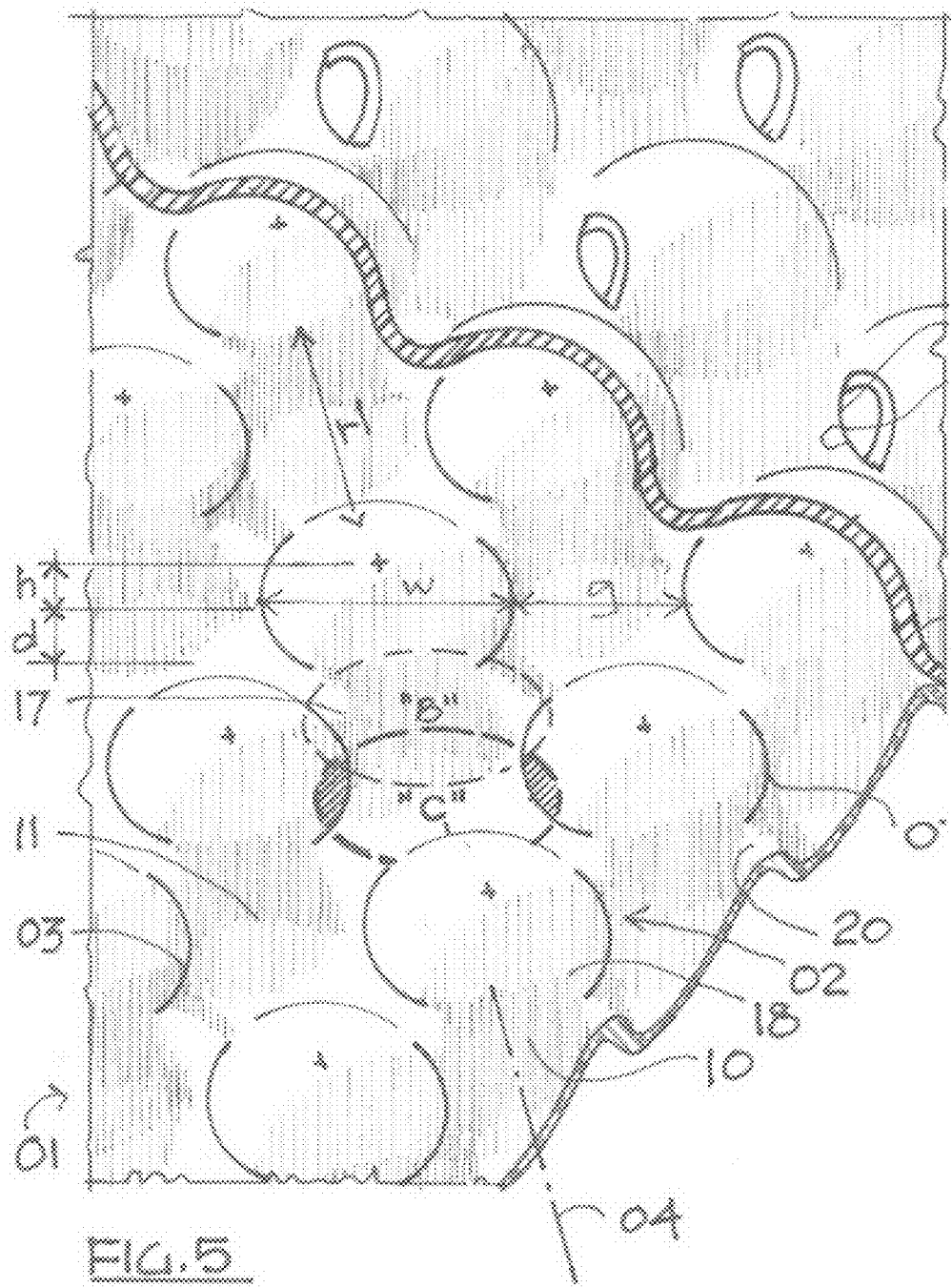
Figure 5A:
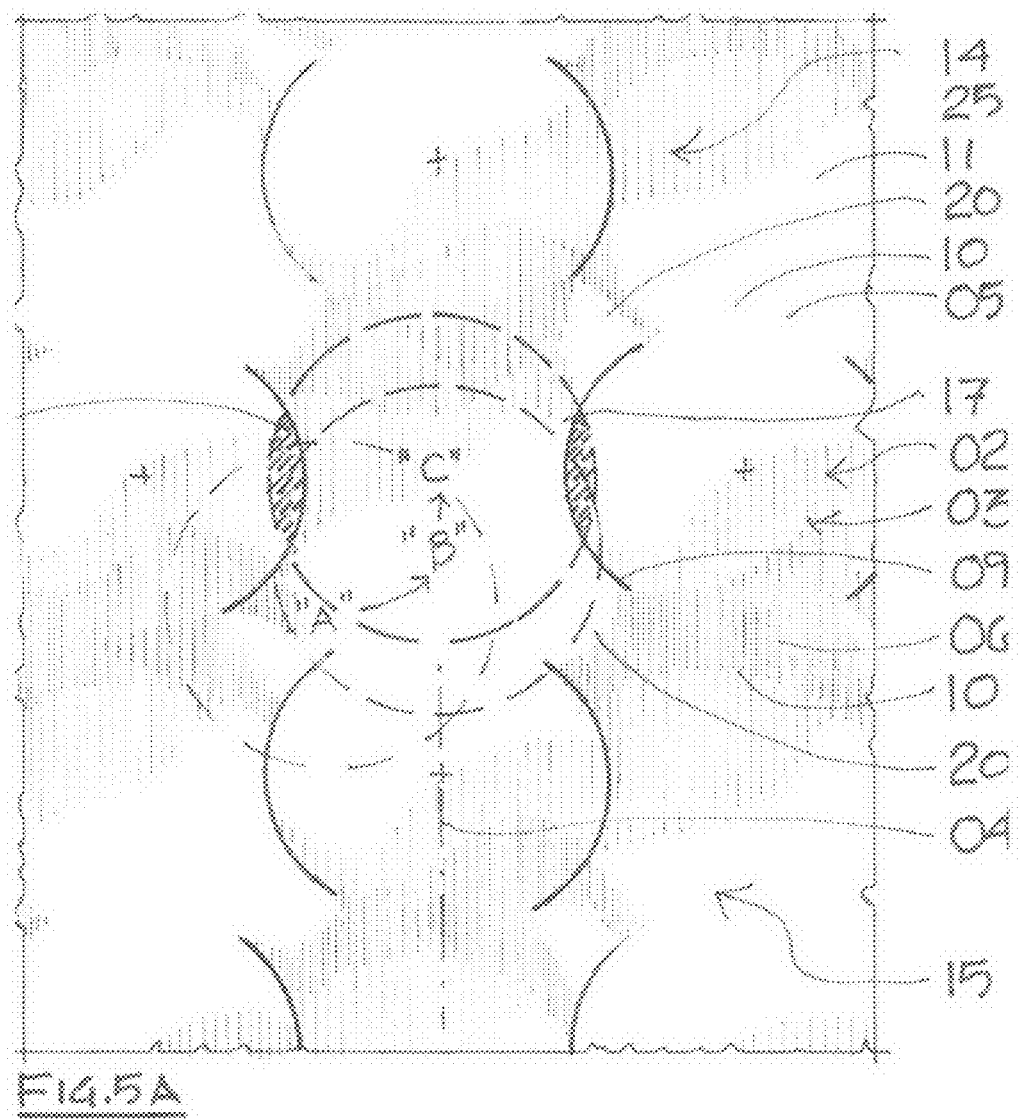

FIG. 5 schematically represents an alternative preferred embodiment with minimal adjustment interval in an oblique view. FIG. 5A is a detail of FIG. 5 in plan view.

Figure 6:
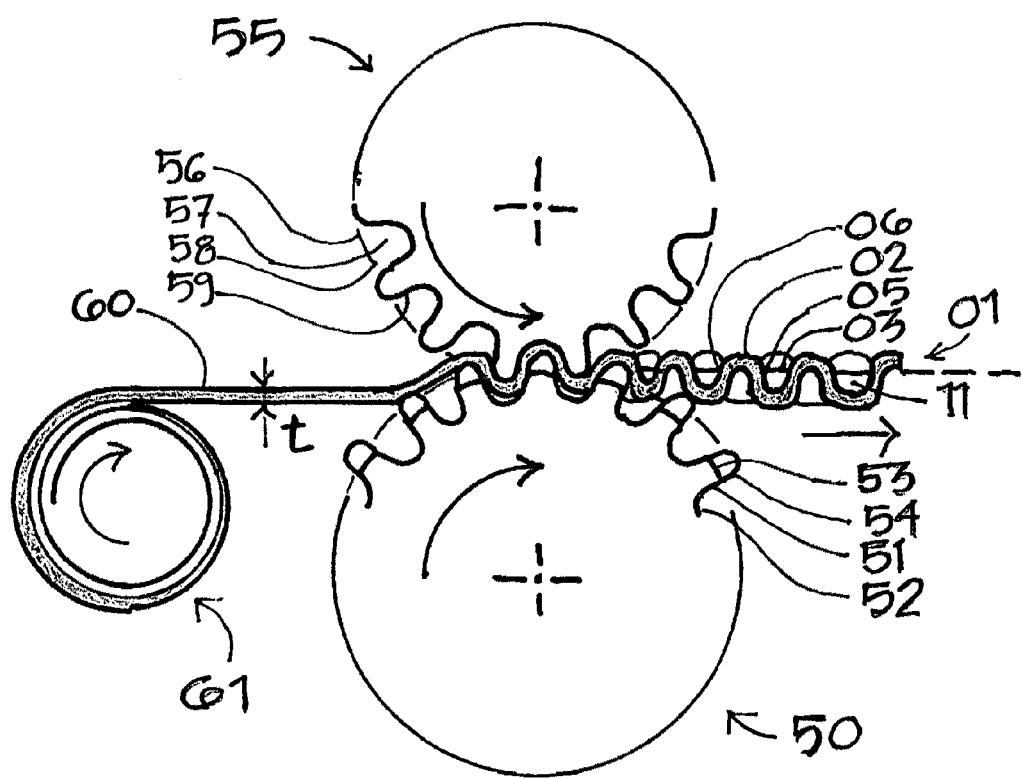

FIG. 6 schematically represents in sectional view a preferred apparatus for manufacturing a touch fastener portion.

DESCRIPTION

As seen in FIGS. 1-5, the Touch Engageable Fastener in diverse embodiments includes two like portions 01, 01' each having a plurality of protrusions 02 arrayed in a first row 13 of at least two such protrusions. Each protrusion has bilateral generally convex sidewalls 18 terminating at undercut edges 03 which are arcuately bowed away from a longitudinal axis 04, and which have undersides 07. The undercut edges are separated by first stems 05 and second stems 06 longitudinally contiguous with the generally convex sidewalls 18, interconnecting protrusions at fore and aft ends respectively. The axis 04 and bilateral undersides 07 of each protrusion are generally coincident with a meeting plane 08. The stems 05, 06 each have stem walls 10 contiguous with the sidewalls 18 which continue below the meeting plane and have stem edges 09.

Embodiments of the invention are described herein as though oriented on common orthogonal width, length, height axes, although such terms are intended to be descriptive in a relative sense only. The term "touch" as used herein is intended to imply the application of a relatively light compressive pressure comparative to the scale of the device: in small scale embodiments such as personal products "touch" implies finger pressure sufficient to engage a segment of the portions without conveying significant distortion on the assembly as a whole or on a substrate; in larger scale embodiments proportionally greater pressure may be required as a matter of design choice. The term "generally convex" is intended to include any shape that fulfills the function of three-dimensionally directing protrusions into corresponding respective receptor openings. Therefore, within the scope of the invention, protrusions may be manufactured with diverse geometries and profile curves which generally have a wider base than top including conical, prismatic, revolved curves, pyramidal shapes, and truncations or combinations of such shapes. The term "arcuately bowed" with respect to the undercut edges of protrusions is intended to include a curved line, two or more conjoined straight line segments, and/or conjoined straight and curved line segments, provided that the edges of a protrusion are closer at a point adjacent to at least the first stem than at the widest lateral section of the protrusion.

At least one receptor 11 is bounded laterally by the stem edges 09 of at least the first stems 05, bounded vertically by the undersides 07 of two laterally adjacent protrusions, and is bounded longitudinally by an oblique stem wall 10 of at least one next proximate protrusion 14 in an adjoining proximate row 21. The stem wall 10 is generally oblique to a basal surface 16 and preferably follows a concave profile generally complementary to the convex profile of a corresponding protrusion sidewall 18. As seen in FIGS. 1-5, the stem wall inclines generally into the receptor from the meeting plane, although segments at and near to the meeting plane may be vertical. The term "oblique", in reference to stem walls, is intended to include diverse curvatures which serve to direct protrusions into their interlocking disposition, preferably mimicking the general convexity of a protrusion profile.

Each receptor 11 has a receptor opening 17, coincident with the meeting plane 08, which is bounded by the undercut edges 03 of two laterally adjacent protrusions 02 and by a stem wall 10 of at least one next proximate protrusion 14 of one longitudinally adjacent row 21. The effective planar profile of a receptor opening 17 generally corresponds to the profile of a corresponding protrusion 02 at the meeting plane, so that a relatively minimal compressive force (touch) will cause the protrusion to "snuggly" enter the opening without causing significant structural distortion of the structure as a whole. It is important to note that the receptors 11 generally comprise a cavity which is at least somewhat larger than a corresponding protrusion 02: extending longitudinally from the stem wall 10 of at least one proximate protrusion 14, effecting a receptor length rl; and extending vertically from undersides 07 to a basal surface 16, depth d; and having an optimally interlocked position vertically opposite the protrusion undersides 07, indicated as hatched area 25. Thus, the receptor openings 17 are inherently offset longitudinally from the protrusion undersides, in that they are coincident with the meeting plane 08 at the relatively lowest horizontal profile between sets of surrounding convex sidewalls 18.

The term "snuggly" is intended to imply a tight but not overly restrictive relationship and may include protrusion profiles and receptor openings of effectively equal size as well as receptor openings somewhat smaller than protrusion profiles. Touch Fasteners of a first type as schematically illustrated in FIGS. 1 and 4 are designed with receptor openings essentially equal in size to a protrusion profile so that the protrusions may enter snuggly but unimpeded. Touch Fasteners of a second type, as will be seen in FIGS. 2, 3 and 5, are designed with somewhat smaller receptor openings so that respective interfacing protrusion sidewalls 18 must be temporarily distorted at their edges 03 as they enter receptor openings 17, then resiliently resume their original shape, thereby effecting a "snap" reception aspect. The aspect of "snugness" is generally determined by the longitudinal spacing of proximate rows of protrusions.

The Touch Fastener is configured so that: the vertical depth "d" of a receptor 11 from the meeting plane 8 to its basal surface 16 is at least slightly greater than the height "h" of a protrusion 02 above the plane; the lateral width "w" between the undercut edges 03 of a protrusion is greater than the gap distance "g" between the edges 03 of adjacent protrusions 02; and the width "s" of a receptor 11, between the stem edges 09 of at least the first stems 05 of laterally adjacent protrusions 02, is at least as great as the width "w" of a corresponding protrusion.

The two portions are fastened together by a method which includes:

1. Providing two oppositely oriented portions 01, 01';
2. Lightly compressing the portions together into initial contact (at a position "A");
3. Continuing compression so as to cause opposing protrusions 02 to bypass as their interfacing surfaces slide laterally and/or longitudinally along respective inclines on a generally convex interface 12 until they each generally self-align with a respective receptor opening 17 (at position "B");
4. Continuing compression so as to cause the protrusions 02 to each be snuggly received into corresponding receptor openings 17 as the respective undercut edges 03 bypass each other;
5. Finally, continuing compression so as to cause respective corresponding oblique stem walls 10 to interface with the obliquely sloping protrusion sidewalls 18 so as to cause the protrusions to shift in a longitudinal direction, effectively entrapping respective corresponding undersides 07 in a generally vertically opposing juxtaposition within the receptor 11 (at position "C"), thereby effectively interlocking the portions.

It is important to note that the dimensional differential specified above regarding receptor depth "d" being at least somewhat greater than protrusion height "h" is an important inherent aspect of the invention. After corresponding respective undercut edges 03 have bypassed the receptor opening at the meeting plane, protrusion sidewalls 18 then continue to effectively shift obliquely along their respective interfacing stem walls 10, simultaneously moving both vertically and longitudinally so as to cause the respective undersides 07 to effectively interlock as they move longitudinally under each other. A d>h differential is necessary in order to allow this essential interlocking action without requiring application of an additional shearing force. As will be seen below, the d>h aspect is also important to the function of fasteners of the "snap" type by providing space for corresponding resiliently distorted undercut edges to bypass as they shift longitudinally. This dimensional differential may be relatively small in many embodiments, but is essential to effect an interlock solely by compression.

Additional applied shearing pressure and/or torsional shifting of the assembly may cause individual protrusions 02 to move longitudinally within their respective receptors while their corresponding undersides 07 generally remain at least partially interfaced. Thereby, the assembly allows for significant flexure without causing the portions to inadvertently disconnect.

Although when thus engaged the assembly is effectively resistant to multi-directional shear, tensile stresses, and torsion, the interlocked assembly may be peeled apart relatively easily by initially separating the portions 01, 01' at an unattached end 19. Lifting the end 19 of an attached portion causes the nearest interfacing undersides 7 to begin to separate at its nearest end, adjacent to a stem edge 09. As further peeling force is applied, the undercut edges 03 readily bypass as the protrusions 02, are sequentially withdrawn through their respective receptor openings 17. Thus, the portions are fully separated, ready for repositioning or removal. As used herein, the term "tension" or "tensile force" is intended to imply a relative perpendicular force generally acting on the structure as a whole. The term "peeling" is intended to imply application of a relative perpendicular force at a portion end so as to sequentially pull the portions apart.

The first preferred embodiment schematically illustrated in FIG. 1 includes a first portion 01 with a plurality of generally dome-like protrusions 02 arrayed in a quadrille pattern of generally aligned rows and columns which define a corresponding plurality of receptor openings 17 between each quadrille set of protrusions and a receptor between each adjacent pair of protrusions. The protrusions are generally circular in planar profile and include undercut edges 03 arcuately bowing away from the longitudinal axis 04, and extending from a relatively narrow first stem 05 to a relatively wider second stem 06. The receptor width "s2" between the edges 12 of the second stems 06 of laterally adjacent protrusions is at least as wide as a first stem 05 and less wide than a second stem 06, thereby effecting a longitudinally asymmetrical design. The receptor opening is sized to just snuggly receive the horizontal profile of a protrusion 02' of second portion 01' without restriction. The oblique stem walls 10 of the next proximate protrusions 14 are located so as to each interface with a segment of sidewall 18 of the second protrusion 02 and thereby direct the protrusion longitudinally into the receptor 11 where it is effectively entrapped by the respective interfacing underside 7 and by the edges 12 of the second stems 06 at an optimal interlocking position 25.

As seen in Diagonal Cross Section B-B of FIG. 1B, the oblique stem walls 10 are concave in profile, generally complementary to protrusion sidewall 18 though with a larger radius, so as to guide the interfacing protrusion into its interlocking position with minimal compressive pressure. An applied uni-directional shearing force is resisted by second stem edges 09 interfacing with the arcuately bowed undercut edges 03' of each respective protrusion/receptor set. If the direction of the shearing force is reversed, the force is initially resisted by stem walls 10 interfacing with protrusion sidewalls 18, though continuing such reverse shearing pressure may ultimately cause the assembly to disengage, as aft protrusion sidewalls 18' obliquely interface and shift vertically along the next proximate second stem walls 10. Therefore, such a longitudinally asymmetrical design is preferred for applications having a generally consistent uni-directional shear stress, as may be furnished by an elastic segment, gravity, etc.

The structure of this first preferred embodiment can be seen to have a generally uniform thickness "t", thereby effecting the essentially thin shell aspect of the device. Such a structure is preferably die-formed from a plastic sheet material with sufficient shape memory to retain the essential three-dimensional elements of the device after forming. A preferred method of manufacture is discussed later in this disclosure. This thin shell aspect, in appropriate materials, allows the structure to be relatively flexible, in that the essentially planar base can flex in multiple directions whilst the three-dimensional aspect of the individual protrusions remains relatively constant. As the structure is flexed within reasonable limits, the interior dimensions of individual receptors may vary without significantly affecting the overall integrity of the connection because individual entrapped protrusions can move within their generally larger receptors and a sufficient number of protrusion/receptor sets remain interlocked at all times to maintain the integrity of the assembly, until it is deliberately peeled apart.

The type of embodiment schematically illustrated in FIG. 1 includes receptor openings 17 with a planar profile at the meeting plane 08 of effectively the same size as the planar profile of a corresponding protrusion 02. Therefore, in embodiments of this first type, a protrusion 03 just snuggly passes through a corresponding respective receptor opening 11 without requiring any additional compressive force beyond minimal touch to initiate engagement of the portions. Therefore this type of embodiment is primarily useful for applications resisting uni-directional shear stresses and requiring minimal attachment pressure. Such applications include overlapping portions having a relatively constant shear pressure maintained by an elastic segment elsewhere in the overlapping structure such as in a binding strap or enwrapping garment article with an integral elastic segment located between the opposing fastening portions. A hanging device activated by gravity along the longitudinal axis would exemplify another potential application. Advantages of this type of embodiment include that it provides high shear resistance and an effectively silent closure/separation action while requiring only minimal "touch" pressure to activate.

A representative example of an embodiment of the type schematically illustrated in FIG. 1 includes dome-like protrusions at a relatively small scale of ±0.10" diameter or less, die formed of a relatively thin ±0.01" thick (t) or less plastic film (such as high density polyethylene). The attached assembly would therefore be approximately 0.125" thick (h+d+2t). The preferred material is generally flexible and at least minimally resilient and has sufficient shape memory to retain its three-dimensional form. A touch engageable device such as this, comparable in scale to molded hook-and-loop, has potentially significant advantages over hook-and-loop including lower production cost, a smooth non-grabbing surface texture, hermaphrodicity, and silent operation; attributes which may be particularly useful for disposable products and packaging. Embodiments at other scales and of other materials will have particular advantages for many distinct application categories.

A second type of embodiment with an alternative configuration is schematically illustrated in FIG. 2. This embodiment includes the essential protrusions 02 and receptors 11 as outlined above, and also has a planar receptor opening profile which at the meeting plane is somewhat smaller in at least one dimension than a respective protrusion profile. Therefore, engaging the portions requires a compressive force sufficient to cause the respective protrusion sidewalls 18 to temporarily deform so as to allow entry of a protrusion into a receptor, thereby effecting a "snap" fit. Such a "snap" aspect can also be optionally applied to embodiments generally configured as in FIG. 1 by simply reducing the distance between successive rows 13, 14, 15, as will be seen in subsequent embodiments below.

The embodiment illustrated in FIG. 2 also includes a longitudinally symmetrical aspect, comprising first and second stems 05 and 06 which are of generally similar width and protrusions 02 in each proximate row which are laterally offset to alternately align with receptors 11, thereby defining receptors which are bounded longitudinally by the oblique stem walls 10 of each proximate row 13, 15, and which are bounded laterally by the stem edges 09 of each laterally adjacent protrusion. Therefore, as relative compression is applied, resilient sidewalls 18 of both corresponding interfacing protrusions 02, 02' are forcibly deformed temporarily in order to allow their respective undercut edges 03, 03' to bypass each other. As the edges bypass and the sidewalls resiliently assume their approximate original shape, the protrusions are effectively entrapped in their respective receptors, confined longitudinally by the oblique stem walls 10 of the next 14 and last 15 proximate protrusions. The portions may be separated by peeling in a fashion similar to that described above.

Embodiments of such a longitudinally symmetrical configuration have an optimal interlocking position 25 where protrusions of both portions 01, 01' are laterally aligned. However, the portions remain in an effectively interlocked disposition, position "C", even when less than optimally aligned.

It should be appreciated that embodiments with rows of alternately offset protrusion, as in FIGS. 2, 3, and 5 and applicable to any embodiment, generally have an inherently shorter adjustment interval spacing. As can be seen in the diverse embodiments, altering proportions and combining aspects by design, within the invention's general parameters, can provide diverse functional attributes to solve particular application requirements.

The preferred embodiment of FIG. 2 also includes protrusions which have a generally polygonal outline at the meeting plane 08 and have a generally pyramidal vertical profile, effectively generally convex as defined above. The protrusions illustrated in FIG. 2 also can be seen to have a shorter height to width aspect (h/w) than those of FIG. 1, which aspect can be varied significantly within the scope of the invention to provide fastener portions with relatively lower or higher profile, smoother or harsher texture, and/or unforced or restricted closure.

It is important to appreciate that the present invention includes a significant range of potential geometric diversity in the configuration of its elements. It is also important to note that the device is fully scalable through a wide range of design choice, limited only by material characteristics and manufacturing method. Several alternative configurations are schematically illustrated in FIGS. 3, 4, and 5 by way of example.

The embodiment of FIG. 3 includes a Touch Fastener with a longitudinally symmetrical aspect as described above, in which the protrusions 02 are laterally elongated, having a width greater than their length so as to effect a generally elliptical planar profile at the meeting plane. This embodiment also includes protrusions 02, 14, 15 arrayed in alternately offset rows 13, 21 which are spaced apart by a minimal distance so as to effect a "snap" fit, wherein the leading undercut edges 03 are forcibly distorted to allow entry into corresponding receptor openings 17. The embodiment of FIG. 3 includes protrusions 02 with undercut edges 03, receptors 11, and receptor openings 17, as in other embodiments. The stem walls 10 are generally concave in at least their longitudinal profile as seen in FIG. 3B, with a curvature of somewhat greater radius than that of a corresponding protrusion sidewall 18. Therefore, a protrusion sidewall 18 interfacing such a generally concave stem wall 10 is directed longitudinally, from position "B" to position "C", into its effectively engaged position by the application of relative compression on the portions. An embodiment of this type, with protrusions of a relatively wide width to length proportion, provides a relatively short adjustment interval which may be advantageous for many applications.

It should also be noted that the embodiment illustrated in FIG. 3 comprises a generally undulating structure which includes "saddle" segments 20 at an intermediate level between the meeting plane and basal surface. This undulation aspect can be seen in FIGS. 3A, 3B, and in the relative contours 23, numbered 0-8, seen in the upper left quadrant of FIG. 3. This optional aspect allows the structure to flex generally along a midplane which is generally coincident with such an intermediate level; thereby providing a relatively high degree of flexure to the whole while the relative dimensions of protrusions and receptor openings remain generally constant. In comparison, embodiments as in FIGS. 1 and 2, with protrusions effectively extending upward from a generally uniform basal surface, will have receptor openings of relatively greater variability in size during flexure of the structure because the distance between protrusions at the meeting plane varies. A further benefit of this undulating aspect is that such fastener portions can be manufactured of a sheet material, as will be discussed, with relatively minimal stress on the material as it is stretched over a forming die.

The embodiment schematically illustrated in FIG. 4 comprises a touch fastener with a longitudinally asymmetrical aspect in which the protrusions are proportionally long relative to their width. It includes protrusions 02 with undercut edges 03, receptors 11, and receptor openings 17 arranged in aligned rows to effect a quadrille pattern. Effectively concave stem walls 10 direct protrusion sidewalls 18 into corresponding respective receptors 11. The aspect of relatively long protrusions in such an asymmetrical embodiment provides a relatively greater engagement area 25 of interfacing protrusion undersides 07 (shown hatched), thereby offering relatively greater tensile resistance as well as uni-directional shear resistance. This aspect may be optionally combined with receptor openings of either the snug or snap types, as noted above.

It should be noted that, in embodiments arranged in a quadrille pattern such as in FIGS. 1 and 3, the actuating interface 12 of sidewalls 18 to pairs of stem walls 10 occurs in a direction which is oblique to the longitudinal axis 04 (diagonal sides, "shoulders" of the stem walls); whereas in embodiments with alternately offset rows such as in FIGS. 2 and 4 the interface 12 generally aligns with the axis 04.

It should be noted that the embodiment of FIG. 4 also includes an optional aspect in which the meeting plane 08 of each row is oblique to the basal surface 16. As seen in FIG. 4B, the leading segment of the undercut edges 03 adjacent to first stems 05 is relatively higher than the trailing edges 03 adjacent to the second stems 06. As in prior embodiments, the depth d of the receptor at this leading edge, next to first stem 05 is at least somewhat greater than the height h of a corresponding protrusion so that sidewalls 18 can obliquely slide along respective corresponding stem walls 10 after passing through the receptor opening 17, (and so that the corresponding undercut edges 03 can fully bypass, and resiliently re-expand in designs also having a snap aspect). However, in this embodiment, the depth of the receptor adjacent to the second stems 06 is approximately equal to the protrusion height so as to effect a wedge-like engagement aspect in vertical section, though the average receptor depth remains greater than the average protrusion height. This optional non-parallel meeting plane aspect can be advantageous in that protrusions may be more easily received into their respective receptor openings and frictional contact between the engaged undersides in their fully "wedged" position resists inadvertent release in the absence of a consistent unidirectional shear pressure.

The embodiment of FIG. 4 also includes optional longitudinal saddles 20 which extend between the ends of adjacent stem walls 05 and 06. In comparison with the embodiment of FIG. 3 above, the saddles 20 here help retain lateral flexibility and three dimensional structural integrity of the structure while minimizing and effectively stiffening the structure longitudinally. It should be appreciated that varying the relative proportions of elements within the general geometric and functional parameters of the invention can result in a wide variety of application specific designs.

FIG. 5 schematically illustrates an embodiment having first 01 and second 01' portions each with a generally undulating structure, including a plurality of dome-like protrusions 02 and generally concave receptors 11. The portions are illustrated in an assembled juxtaposition with the second portion 01' viewed from its underside. Embodiment of this type are designed to minimize the longitudinal adjustment interval, and to minimize movement of protrusions within their receptors. It is similar to previous embodiments of the longitudinally symmetrical "snap"—type as seen in FIGS. 2 and 3, with a receptor depth d somewhat greater than the protrusion height h, a protrusion width w greater than the gap g between adjacent undercut edges, and with rows of alternately offset protrusions. However, the embodiment of FIG. 5 is configured so that the protrusion width w is larger than gap g between adjacent undercut edges by a relatively small differential to facilitate "snap", and the receptor length rl between a next 14 and last 15 proximate protrusions in their respective next proximate rows is relatively short, so that the concave profile of proximate stem walls and basal surface closely approximates the longitudinal profile of a corresponding protrusion. Therefore, the engaged position "C" closely approximates the optimal interlocking position 25: although the area of engaging undersides 07 is relatively small, the close-coupling of protrusions within their respective receptors provides a secure interlock.

As seen in FIGS. 5 and 5A, the receptor openings 17 (position "B") are closely offset from their respective underlying receptors 11 (position "C"). Therefore upon application of relative compression: 1) protrusions 02 are first directed into alignment with corresponding receptor openings 17 as respective convex protrusion sidewalls of the first and second portions interface and are guided into their lowest possible alignment prior to deformation of the respective undercut edges 03, at a receptor opening 17 which is slightly offset longitudinally from the receptor center below; 2) As compression continues, respective corresponding sidewalls 18 adjacent to undercut edges 03 resiliently deform to allow passage of protrusions 02 into their corresponding receptors 11; and 3) As the temporarily deformed protrusions 02 pass through the receptor openings 17, a next proximate protrusion sidewall 18 simultaneously interfaces with the nearest next proximate stem wall 10 so as to direct the protrusion into its corresponding receptor as the lateral sidewalls 18 at the undercut edges resiliently resume their original shape, thereby interlocking the portions with undersides 07 oppositely disposed. It is important to understand that, even in this type of "close-coupled" embodiment, as the protrusions 02 approach their corresponding receptor openings, in step 1) above, they are directed into an alignment which is at least slightly offset longitudinally from the centerline of the receptor (a receptor opening is always defined by two adjacent actuate undercut edges and at least one proximate stem wall in the nearest proximate row). It is also important to understand that here as in other embodiments the depth of receptors is inherently deeper that the height of a corresponding protrusion so as to allow protrusions 02 to longitudinally shift into their receptors 11 as their respective undercut edges 03 simultaneously bypass.

It should be understood that, as in all embodiments, the engaged protrusions are free to move within the boundaries of their respective receptors unless restrained by an applied shear or tensile force. In the embodiment of FIG. 5 longitudinal movement is relatively closely restricted, although there is somewhat greater freedom to move in a vertical direction, whereas in other embodiments such as in FIG. 3 above, relatively greater longitudinal movement is allowed relative to vertical movement. This aspect, variable by design choice, is generally beneficial in that it allows significant flexure of the whole without causing disconnection of individual elements.

The embodiment of FIG. 5 also includes a relatively thin shell structure with diagonally disposed saddles 20 allowing flexure of the structure along a midplane coincident with the saddles without significant variation in relative protrusion and receptor dimensions. Such an embodiment, with its short adjustment interval and effectively tight engagement fit, can be highly useful for many applications and, like other embodiments, may be economically manufactured by die forming inexpensive materials with the preferred method and apparatus specified below.

For many applications, a first portion 01 may be provided as a relatively larger field or target area, whilst the second portion 01' may be somewhat smaller in area (ideally about thumb size for apparel-type items) for adjustable placement at a desired location on the field, thereby maximizing two dimensional adjustability. The device is preferably designed so that it should not be generally necessary to connect all of the domes of both portions, since redundancy of the relatively strong interlocked domes should provide adequate strength in most instances even when a relatively large percentage are not fully connected. An end tab is preferably provided to at least the edge 19 of the overlapping portion as a grip for removal, graspable between thumb and forefinger. Embodiments of any design may be attached to a substrate by diverse commonly known means such as sewing, stapling, gluing, thermally fusing, etc.

It should be noted that all embodiments have fastening and non-fastening orientations relative to their radial alignment, whereby portions aligned perpendicularly will not interconnect. However, zones of alternately oriented protrusions may be provided in embodiments of symmetrical designs to provide for bi-directional engagement. It should also be noted that fastener portions include fastening orientations and non-fastening orientations relative to their top and bottom surfaces: they can not be produced as inter-engageable portions via either surface because of the above noted differential of receptor depth versus protrusion height and associated proportions. However, embodiments of any design may be produced with a self-engaging aspect by providing a first fastening zone effective from the first surface and, elsewhere along the same structure, a second fastening zone effective from the second surface.

An apparatus and method for manufacturing touch fastener embodiments is schematically illustrated in FIG. 6. For many applications various embodiments of the device may be economically die-cut and formed of a sheet material, including plastics, fibers, paper, sheet metal, etc. by such an apparatus which includes a set of counter-rotating cylindrical dies 50, 55. A first cylindrical die 50 is provided with a geometric array of posts 51 extending from its surface 52, the posts corresponding with the inner shell surface of protrusions 02 in a finished portion 01. Each post has cutting edges 53 corresponding with undercut edges 03 and non cutting surfaces 54 corresponding with stems 05, 06. A second cylindrical die 55 includes a surface 56 perforated by an array of apertures 57 corresponding with the posts, also with cutting edges 58 and non-cutting edges 59 respectively corresponding to undercut edges and stems, with allowance for material thickness t at each stem location. The cylindrical dies 50, 55 are assembled in a counter-rotating configuration so that surfaces 52 and 56 are separated by the thickness t of the sheet material 60 fed from roller 61, and so that posts 51 progressively enter apertures 57 as the cylinders are rotated. Thence, the sheet material 60 is fed into the space between the cylinders and formed into the resulting portion 01 with its arrayed protrusions 02 and intervening receptors 11.

The cylindrical dies may also include forming segments for other features such as optional ribs correspondent with saddles 20 between protrusions as in FIG. 4 above. Likewise, both dies may include both post and aperture elements for forming fasteners with undulating structures such as the embodiment illustrated in FIG. 3. Other features may also include portion cuffing and separating devices identifying devices, etc. Optionally the dies may include zones with reversed die elements for forming self-engaging straps or portions with engagement zones on each surface of the structure.

The apparatus as described above may be used to economically produce fastener portions in a cold-forming process using materials with adequate shape memory to retain their formed three-dimensional aspects after release form the die set. A similar apparatus may be utilized in heat-forming other materials which may require application of heat to form useable fastener products.

Alternative methods of manufacture may include die-sets forming a single or relatively few protrusion rows with a reciprocating press wherein the product may be sequentially moved forward in a continuing process. The device may also be molded by injection molding, or integrally molded as a fastening zone in a larger molded component, by utilizing a set of bypassing dies. An injection molding or extrusion process can produce stronger and more durable fasteners for many applications such as clothing, sports and safety equipment, or various structural applications. Optional embodiments in rubber, rubberized plastics, silicon, foam, even leather or wood are also readily achievable with known manufacturing methods.

A wide range of materials may be utilized which have sufficient shape memory, strength, and flexure. High Density Polyethylene films of thicknesses ranging from 0.005"-0.020" thick have been utilized effectively in cold formed experimental embodiments with module widths of 0.015"-0.25". A material thickness to protrusion width ratio of approximately ⅓-⅛ appears to work well with this material.

Other common plastics have similar characteristics for cold forming. Yet other materials may require application of heat and/or chemical processes.

Having thus described the various aspects of the invention in schematic form, which aspects may be combined and configured in diverse combinations within the scope of the invention, I hereby claim the following:

The invention claimed is:

1. A touch fastener comprising a first portion for attaching to a second portion, said first portion including a generally thin shell structure comprising a continuous undulating three-dimensionally shaped sheet of generally uniform thickness with:
   a plurality of protrusions with generally convex sidewalls, each protrusion having bilaterally undercut edges with undersides coincident with a meeting plane, said edges arcuately arching away from a longitudinal axis, said edges separated by a first stem and a second stem, each stem contiguous with said sidewalls and extending below said meeting plane;
   a receptor between each laterally adjacent pair of said protrusions, said receptor bounded laterally by at least said first stems, bounded vertically by said undersides of adjacent said undercut edges, and bounded longitudinally by at least one next proximate stem wall associated with a next proximate protrusion of a longitudinally adjacent row; and
   a receptor opening, longitudinally offset from said receptor, coincident with said meeting plane, extending between said undercut edges of adjacent protrusions and said at least one next proximate stem wall;
   said protrusions and said receptor configured so that:
      the depth of said receptor below said meeting plane is greater than the height of said protrusions above said meeting plane;
      the width of said protrusion at said meeting plane between said undercut edges is greater than the gap between the undercut edges of laterally adjacent protrusions, and said gap is at least as great as the width of at least said first stem;
      said receptor opening is sized to snuggly receive a respective corresponding protrusion associated with said second portion; and
      said next proximate stem wall is obliquely inclined into said receptor;
   so that application of a relative compressive force to said first and second portions causes at least one protrusion of said second portion to vertically align with and pass through said receptor opening, and thence shift longitudinally into an interlocking juxtaposition as said generally convex sidewalls interface said obliquely inclined stem walls.

2. A touch fastener according to claim 1, wherein the distance between laterally adjacent said second stems is greater than the width of each said first stem and less than the width of each said second stems, whereby said adjacent second stems longitudinally bound said receptor in a direction of primary longitudinal shear resistance.

3. A touch fastener according to claim 2 comprising at least two rows of alternately offset protrusions.

4. A touch fastener according to claim 2 comprising at least two rows of generally aligned protrusions.

5. A touch fastener according to claim 1, wherein said receptor opening is smaller than the profile of a corresponding protrusion, thereby causing respective interfacing sidewalls to resiliently deform upon application of said relative compressive force as said protrusion passes through said receptor opening.

6. A touch fastener according to claim 5 wherein at least said first portion has at least three rows of alternately offset protrusions, and wherein the width of said first stems substantially equals the width of said second stems, and wherein the distance between laterally adjacent said first and second stems is less than the distance between adjacent said undercut edges and greater than the width of said first and second stems, and wherein each said receptor is longitudinally bounded by a second proximate stem wall of the next row of protrusions and by a first proximate stem wall of the last row of protrusions.

7. A touch fastener according to claim 1, wherein each said portion includes a structure of generally uniform material thickness, and wherein said thickness is less than one third the width of each said protrusion.

8. A touch fastener according to claim 1, wherein said protrusions have a generally polygonal planar profile at said meeting plane.

9. A touch fastener according to claim 1, wherein said protrusions have a generally curvilinear planar profile at said meeting plane.

10. A touch fastener according to claim 1, manufactured of a generally resilient material.

11. A touch fastener according to claim 1, wherein said protrusions have a longitudinal dimension greater than their lateral dimension at the meeting plane.

12. A touch fastener according to claim 1, wherein said protrusions have lateral dimension greater than their longitudinal dimension at the meeting plane.

13. A touch fastener according to claim 1, manufactured of a generally sheet form plastic material by an apparatus including a set of cutting and forming dies.

14. A method for attaching a first portion to a second portion comprising the steps of:
   providing a touch fastener according to claim 1;
   arranging said first portion in an opposite orientation with said second portion;
   applying a relative compressive force to the portions so that at least one protrusion of said first portion shifts into alignment with and enters at least one respective corresponding receptor opening of said second portion and vice versa;
   continuing said force so that a sidewall of said one protrusion interfaces with a proximate stem wall and shifts longitudinally along said interface into its corresponding respective receptor;
   thereby attaching the portions.

15. A touch fastener according to claim 1, wherein said meeting plane is oblique to a horizontal basal surface.

16. A touch fastening portion comprising a generally thin shell structure with a continuous undulating three-dimensionally shaped sheet of generally uniform thickness, further comprising a plurality of receptors for receiving at least one generally convex second protrusion, said receptors each comprising a chamber defined by:
   bilaterally disposed pairs of first and second stem edges
   a pair of bilaterally disposed undersides with undercut edges generally coincident with a meeting plane and arcuately bowing from a parallel pair of longitudinal axes;
   at least one obliquely inclined proximate stem wall of a next proximate protrusion; and
   a receptor opening at said meeting plane defined by said undercut edges and said at least one stem wall, for snuggly receiving said second protrusion;
wherein laterally adjacent said receptors are each separated by a generally convex first protrusion extending above said meeting plane, and wherein the distance between said at least said first stem edges is greater than the distance between said undercut edges, the distance between laterally adjacent said undercut edges is less than the distance between the undercut edges of said first protrusion, and the depth of said receptor is grater than the height of said protrusion as measured from said meeting plane.

17. A touch fastener according to claim 16, wherein the distance between laterally adjacent said second stems is greater than the width of each said first stem and less than the width of each said second stems, whereby said adjacent second stems longitudinally bound said receptor in a direction of primary longitudinal shear resistance.

18. A touch fastener according to claim 16, wherein said receptor opening is smaller than the planar profile of a corresponding protrusion at said meeting plane, thereby causing respective interfacing sidewalls to resiliently deform upon application of said relative compressive force as said protrusion passes through said receptor opening.

19. A touch fastener according to claim 18, wherein at least said first portion has at least three rows of alternately offset protrusions, and wherein the width of said first stems substantially equals the width of said second stems, and wherein the distance between laterally adjacent said first and second stems is less than the distance between adjacent said undercut edges and greater than the width of said first and second stems, and wherein each said receptor is longitudinally bounded by a second proximate stem wall of the next row of protrusions and by a first proximate stem wall of the last row of protrusions.

20. A fastening device which includes a generally thin shell structure comprising a continuous undulating three-dimensionally shaped sheet of generally uniform thickness comprising:
  a first portion for attaching with a corresponding second portion, said second portion including:
    a plurality of dome-like protrusions arrayed in rows;
  each said protrusion having:
    generally convex sidewalls leading to
    bilateral undersides arcuately bowing away from a longitudinal axis and coincident with a meeting plane,
    longitudinally opposite first and second stems between said undersides,
    each with continuous stem walls continuing below said meeting plane, said protrusions configured so that:
      the width of at least said first stems is less than the gap between said undercut edges of adjacent said protrusions;
    said rows of protrusions arranged so that a corresponding respective protrusion of the first portion is snuggly received within a receptor opening defined by said edges of adjacent undersides and the proximate stem wall of at least one protrusion in the next proximate row; and
  a receptor between each said protrusion, longitudinally offset from a receptor opening, defined by:
    an adjacent pair of said undersides,
    laterally adjacent said first and second stems,
    at least one longitudinally adjacent oblique stem wall of a next proximate protrusion of a next proximate row;
    said receptor having a depth from said meeting plane greater than the height of a corresponding protrusion;
  so that application of a relative compressive force on oppositely disposed portions initially causes generally convex protrusions of the first portion to slide laterally and longitudinally along said sidewalls into alignment with said receptor openings of said second portion, and vice versa, thence upon further compression, causes said protrusions to enter said receptor openings so as to interface with said oblique stem wall, thereby causing said protrusions to glide longitudinally into an engaged disposition within said receptors wherein the undersides of corresponding respective protrusions effectively interface, thereby attaching the portions.

21. A method for attaching two portions comprising:
  providing the two portions as in claim 1;
  orienting the longitudinal axis of each portion in a generally parallel juxtaposition;
  applying a relative compressive force to align said at least one said protrusion with a respective corresponding receptor opening;
  applying additional relative compressive force to engage the portions by slidingly interfacing said sidewall along said stem wall of said next proximate protrusion;
thereby attaching the portions.

22. A touch fastener according to claim 1 manufactured by a method including the steps of:
  providing an apparatus including a set of counter rotating dies, at least one of said dies including a plurality of punching and forming posts, and at least one of said dies including a plurality of cutting and forming apertures for receiving said posts;
  inserting a deformable plastic sheet with inherent shape memory between said dies;
  rotating said dies so as to cut and form said substance to produce portions of said touch fastener.

\* \* \* \* \*